United States Patent [19]

Butland

[11] Patent Number: 4,660,799

[45] Date of Patent: Apr. 28, 1987

[54] LOAD SUPPORT STRUCTURE

[76] Inventor: Edward H. Butland, 11746 Thunderbird Ave., Northridge, Calif. 91326

[21] Appl. No.: 823,958

[22] Filed: Jan. 29, 1986

[51] Int. Cl.[4] ............................................. F16M 3/00
[52] U.S. Cl. ..................................... 248/676; 52/39; 52/90; 52/648; 248/317; 378/193
[58] Field of Search ............... 248/676, 678, 127, 660, 248/183, 317, 323; 378/193, 195; 211/182, 184; 52/648, 656, 74, 78, 79.12, 90, 39

[56] References Cited

U.S. PATENT DOCUMENTS

| | | | |
|---|---|---|---|
| 2,737,596 | 3/1956 | Haupt et al. | 378/197 X |
| 3,373,285 | 3/1968 | Barrett | 378/197 X |
| 4,041,657 | 8/1977 | Schuplin | 52/39 |
| 4,191,356 | 3/1980 | Ashmun et al. | 248/678 |
| 4,364,695 | 12/1982 | Lenz | 248/676 X |

Primary Examiner—Ramon O. Ramirez
Attorney, Agent, or Firm—Robert J. Schaap

[57] ABSTRACT

A load supporting structure primarily for supporting X-ray apparatus in the form of a free standing unit which can be packaged as a kit and assembled at an on-site location. The load supporting structure comprises a pair of spaced apart longitudinally extending first beams with a plurality of spaced apart transversely extending second beams connected to the longitudinally extending first beams. The longitudinally extending beams are supported by a plurality of upright columns. The X-ray apparatus is supported on the transversely extending beams and is shiftable therealong. The distance between the transversely extending beams can be easily adjusted in order to compensate for the dimensions of the X-ray apparatus.

20 Claims, 6 Drawing Figures

LOAD SUPPORT STRUCTURE

BACKGROUND OF THE INVENTION

1. Field of the Invention

This invention relates in general to certain new and useful improvements in load supporting structures, and more particularly, to load supporting structures of the type capable of supporting an X-ray apparatus in a suspended position and which are of short spans and capable of being provided in a pre-packaged form and assembled at an on-site location.

2. Brief Description of the Prior Art

X-ray apparatus are frequently used in many medical facilities such as physicians office, hospitals and the like. The X-ray apparatus is generally adapted for overhead mounting such that it is located near or adjacent to the ceiling of a room or other enclosed environment.

The X-ray apparatus usually includes a frame for supporting a housing containing the X-ray tube. This housing is usually suspended and shiftable vertically along a vertically disposed frame to a desired height. Moreover, the housing of the X-ray tube and the attendent frame must be capable of being shifted horizontally to a desired location. Due to the fact that the X-ray apparatus itself generally has a substantial weight, in the region of at least 800 to 1000 pounds or more, a fairly substantial supporting structure is required. Due to the substantial weight, the X-ray apparatus cannot be connected to the ceiling panels or ceiling grid.

Heretofore, there has been no standard approach for providing a supporting structure to mount an X-ray apparatus. Due to the fact that there are numerous sources for such X-ray apparatus, there are no industry standards of size or weight. Moreover, each supporting structure is generally treated as a customized project, that is a specific supporting structure is designed at the time that an X-ray apparatus is to be installed. Moreover, the supporting structures will vary depending upon the construction of the building and particularly the construction of the overhead ceiling. As a result, not only is the X-ray apparatus expensive, but the necessity of employing architectural firms to design the supporting structure and engineering companies to construct the supporting structure adds substantially to the overall cost thereof.

The installation of an X-ray apparatus usually requires a substantial amount of architectural and engineering efforts, in a new building construction, as previously described. However, when it is desired to install an X-ray apparatus in an existing room or structure, different engineering considerations are involved. Usually, a substantial amount of re-engineering is performed to modify the existing ceilling structure or overhead floor structure and which again results in substantial engineering costs.

Heretofore, there has not been any supporting structure for X-ray apparatus or other heavy loads which is provided in a pre-packaged or so-called "kit" form along with drawings for erection and assembly at an on-site location.

OBJECTS OF THE INVENTION

It is, therefore, one of the primary objects of the present invention to provide a load supporting structure in pre-packaged form capable of being erected and assembled at an on-site location.

It is another object of the present invention to provide a load supporting structure of the type stated which is designed for supporting X-ray apparatus capable of movement in at least a horizontal direction.

It is a further object of the present invention to provide a load supporting structure of the type stated which is free-standing and does not require a specially built ceiling or overhead floor construction.

It is an additional object of the present invention to provide a load supporting structure of the type stated in which the components thereof are essentially all bolted and do not require other expensive fastening techniques.

It is also an object of the present invention to provide a load supporting structure of the type stated which is capable of being pre-packaged and assembled at an on-site location to substantially reduce the overall cost of X-ray apparatus installation.

It is another salient object of the present invention to provide a load supporting structure of the type stated which can be constructed at a relatively low unit cost and which is highly reliable in its operation.

It is still another object of the present invention to provide a method of assembling a load supporting structure at an on-site location.

With the above and other objects in view, my invention resides in the novel features of form, construction, arrangement and combination of parts presently described and pointed out in the claims.

SUMMARY OF THE DISCLOSURE

An overhead load supporting structure which is capable of being pre-packaged and erected and assembled at an on-site location. This load supporting structure is highly effective for use in supporting small span loads of moderate weight and particularly is highly effective for supporting X-ray apparatus. In this case, a small span is deemed to be a span in the area of about 15 to about 25 feet. Moderate weight loads may range from about 500 pounds to about 2,000 pounds. The average X-ray apparatus including the attendent frame and tube housing weighs about 800 to 1,000 pounds.

The load supporting structure of the present invention comprises a plurality of upright columns, usually four columns, which are adapted to be located in a rectangular arrangement, preferably at the corners of a room. A pair of first beams, which are preferably in the form of C-shaped channels, are connected to pairs of the upright columns in a spaced apart parallel arrangement. The pair of first beams are releasably connected to the columns in such manner that the columns may be spaced apart from each other by a desired dimension and then secured by mechanical fasteners.

At least a pair of secondary beams, often referred to as "second beams" extends between the first beams or C-shaped channels and may be rigidly secured thereto, as hereinafter described. The secondary beams are also spaced apart from each other and in parallel arrangement. Moreover, the secondary beams are preferrably I-beams.

The term "beam" is used in a broad sense to represent essentially any type of horizontally disposed structural member and does not refer to an I-beam as such. Moreover, the term beam is used in a broad sense to encompass other types of horizontal structural members including trusses, channels, such as the C-shaped channels and the like.

In a more preferred embodiment of the present invention, three of the second beams extend between the first beams or C-shaped channels and two of the second beams are designed to secure and carry the X-ray apparatus and the third of the secondary beams is designed to carry cables and the like for the X-ray apparatus.

The present invention provides a means to enable two or more of the second beams such as the I-beams to be movable relative to one another so as to obtain a desired spaced apart arrangement. As indicated previously, X-ray apparatus and particularly the size of the tube housing and the frame therefor, may vary depending upon the manufacturing source thereof. For this purpose, a desired position must be established between a pair of the I-beams in order to receive and retain the X-ray apparatus.

The means to enable the adjustable positioning of the I-beams or second beams comprises one or more first frame members secured to a side of a longitudinally extending first beam and an additional frame or second frame member secured to a side of the second longitudinally extending beam. These first and second frame members co-operate by means of for example, L-shaped brackets which permit a slidable movement of the second beams with respect to the first beams. After the second beams have been positioned in a desired spaced apart arrangement, they can then be secured to the first beams.

In a first aspect, the free standing X-ray apparatus support structure can be considered to comprise a pair of first beams which extend generally parallel to one another in a first direction and a plurality of second beams which extend between the pair of first beams and which are supported thereby. The second beams are also generally parallel to one another in a second direction. The plurality of columns are disposed in generally upright positions and these columns are disposed on and supported by a floor or similar horizontally disposed supporting surface.

This free standing X-ray apparatus support structure also comprises a first framing channel, often referred to as a first "frame member" secured to each of the first beams and a second framing channel or second frame member secured to each of the second beams and which are located at substantially the same horizontal elevation as the first frame member. The second frame member co-operates with the first frame member to enable the second beams to be movable with respect to the first beams. Finally, the free standing X-ray apparatus support structure comprises a locking means for locking the second beams in a desired position with respect to the first beams when a desired spacing has been achieved between the second beams.

This one aspect of the X-ray apparatus support structure preferably comprises a second bracket forming part of the locking means and which extends between the first frame members and the second frame members to enable a locking of the second beams with respect to the pair of the first beams. The locking means also comprises first mechanical fasteners for securing the first beams to the columns and second mechanical fasteners for securing the second beams to the first beams.

In another preferred embodiment, the support structure is rectangularly shaped and is comprised of four upright columns located at the corners of a rectangular arrangement. Furthermore, the height of the columns is preferably vertically adjustable so as to achieve a desirable vertical elevation of the first and second pairs of beams.

In another aspect of the invention, the support structure can be provided in the form of a kit, as previously described. In this case, the various beams and the columns are pre-cut to the desired sizes so that they can be easily assembled at a desired on-site location.

The present invention can be considered as a method before assembling a free standing X-ray apparatus support structure at an on-site location. The method comprises the erecting of a plurality of columns in a selected pattern in upright disposition. Thereafter, the method comprises the securing of the plurality of first beams, which are pre-cut to the desired sizes, to the plurality of columns in a certain horizontal arrangement. Thereafter, a plurality of the second beams, which are also pre-cut to a desired size, are located with respect to the plurality of the first beams and also in a certain horizontal arrangement. In addition, the method comprises movably positioning at least one of the second beams with respect to another of the second beams in order to obtain a desired spacing therebetween and which spacing is sufficient to support and accommodate an X-ray apparatus. Finally, the method comprises the securing of the second beams to the first beams when in the desired horizontal spacing.

The present invention is also highly effective in that it avoids the necessity of using welded securement and the like. Each of the first and second beams are adapted for bolted attachment to one another. Moreover, the beams are also adapted for bolted attachment to the columns. In this way, the entire supporting structure can be easily assembled and disassembled. Further, it can be observed that the supporting structure can be assembled as part of a building which is in the state of being constructed, or it can be installed in an existing structure.

The support structure of the present invention is highly effective for being pre-packaged such that it is not necessary to have elaborate architectural and engineering drawings and the pre-packaged kit containing the components can be cut to desired sizes and shapes based on the specifications provided by the intended user. Moreover, assembly drawings can also be provided. However, inasmuch as the assembly shop drawings are always based upon essentially the same numbers and types of components, they can easily be prepared in an almost standard manner.

This invention possess many other advantages and has other purposes which may be made more clearly apparent from a consideration of the forms in which it may be embodied. These forms are shown in the drawings forming part of and accompanying the present specification. They will now be described in detail for the purposes of illustrating the general principles of the invention, but it is to be understood that such detailed descriptions are not to be taken in a limiting sense.

BRIEF DESCRIPTION OF THE DRAWINGS

Having thus described the invention in general terms, reference will now be made to the accompanying drawings (five sheets) sheets in which:

DETAILED DESCRIPTION OF PREFERRED EMBODIMENTS

Referring now in more detail and by reference characters to the drawings which illustrate preferred embodiments of the present invention, A designates a free standing X-ray apparatus support structure which may be provided in the form of a kit of components and which may be assembled at an on-site location. For the purposes of the present invention, the free standing X-ray apparatus support structure is described in the form of an assembled support structure, but is to be understood that the various components thereof would be pre-cut to the desired sizes and shipped to an on-site location where they may be easily erected and assembled at an on-site location.

Figure 1:
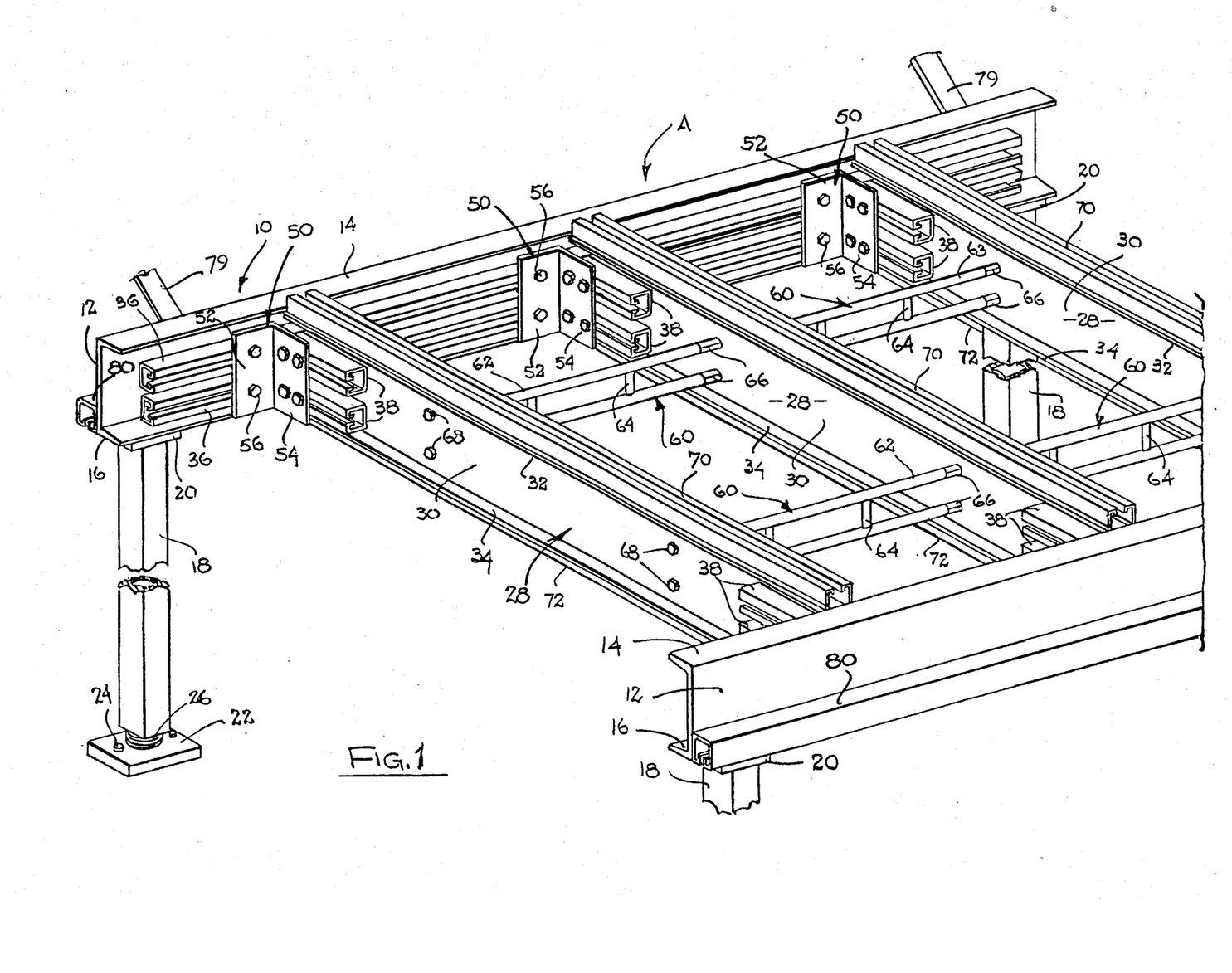
FIG. 1 is a perspective view, partially broken away of an assembled X-ray apparatus support structure constructed in accordance with and embodying the present invention.

Referring now to FIG. 1, it can be observed that the free standing support structure A generally comprises a pair of spaced apart longitudinally extending first beams 10 which are preferably C-shaped channels 10. Each of these channels are preferably comprised of a vertically disposed web 12 integrally provided at the upper and lower ends with inwardly struck flanges 14 and 16, respectively.

The channels or first beams 10 are each supported at their opposite ends by pairs of vertically disposed columns 18. Each of the columns 18 are provided at their upper ends with head plates 20 for engagement with the inwardly struck lower flange 16 of each first beam 10. The means of securement in accordance with the present invention preferably comprises bolts or similar mechanical fasteners which avoids the need for welding and other types of labor intensive securement. The exact means of securing the first beams 10 to the columns 18 is hereinafter described in more detail. At their lower ends the columns 18 are provided with footplates 22 which are also capable of being secured to a floor or similar supporting surface by means of mechanical fasteners 24. In this case, the exact type of mechanical fastener would depend upon the composition of the floor. For example, if the floor were formed of a concrete material, the mechanical fasteners would adopt the form of stud bolts.

Each of the columns 18 are also preferably provided with a conventional height adjustment mechanism 26, in the manner as illustrated in FIG. 1. The pipe adjustment mechanism comprises an externally threaded pipe or similar member which is threadedly disposed within the lower tubular end of the column 18 and is also secured to the foot plate 22 of that column. The pipe or other inner cylindrical member is capable of being threadedly positioned within the column to a desired depth so as to adjust the overall relative height of the column. The height adjustment mechanism may also be located within opposed ends of a column split somewhat intermediate its opposite ends and which pipe is threadedly secured within the opposed parts of the column sections.

Another type of height adjustment mechanism which may be employed in accordance with the present invention is the use of a telescopic column in which one column section is telescopically disposed within another column section and shiftable therein to a desired position so as to achieve an overall height. Dowell pins may be employed in order to secure the two column sections in the desired position. Inasmuch as the height adjustment mechanism 26 is conventional and the other height adjustment mechanisms as described herein are conventional, they are neither illustrated nor described in any further detail herein.

In actual construction, each of the columns would normally be pre-cut to the desired size. The height adjustment mechanisms would be provided to account for slight marginal differences and non-linearities in the relative spacing between the floor and ceiling or for other non-linearities, e.g. in the plane of the floor or similar supporting surface. Also, in the embodiment as illustrated, four such columns are provided in order to create a rectangular support structure. However, it should be understood that the support structure could be of a different shape, such as the shape of a pentagon or the like in order to conform to the environment in which it is to be located.

Connected to the pair of first beams 10 are a plurality of second beams 28 (three as shown) which preferably adopt the form of I-beams, in the manner as illustrated. These I-beams 28 are of conventional construction and each comprises a vertically disposed plate or web 30 having integral upper and lower flanges 32 and 34, respectively. It should be understood that the number of I-beams 28 which are employed, may vary depending upon the type of X-ray apparatus which is to be supported thereby. In most of the conventional X-ray support apparatus, two of the secondary beams or I-beams 28 are provided for carrying the X-ray apparatus housing and a third of the beams 28 is provided for carrying the cables.

The second beams 28 must be properly positioned with respect to the pair of first beams 10 and with respect to each other in order to properly accommodate the X-ray apparatus and the third of the secondary beams 28 must also be properly positioned relative to the other two beams 28 in order to accommodate the necessary length of the cables for this X-ray apparatus. In this case, the term "X-ray apparatus" is deemed to include the cables and auxilary components which must be carried by the support structure of the present invention.

A positioning-locking means is provided for connecting the I-beams or secondary beams 28 to each of the first beams 10. This positioning-locking mechanism comprises a pair of vertically spaced apart framing channels 36 which are welded or otherwise rigidly secured to the interiorly disposed faces of the webs 12, in the manner as illustrated in FIG. 1. A pair of framing channels 38 are similarly secured to the web of each of the beams 28, also in the manner as illustrated in FIG. 1. The framing channels 38 are located at the same height as the framing channels 36.

Figure 3:
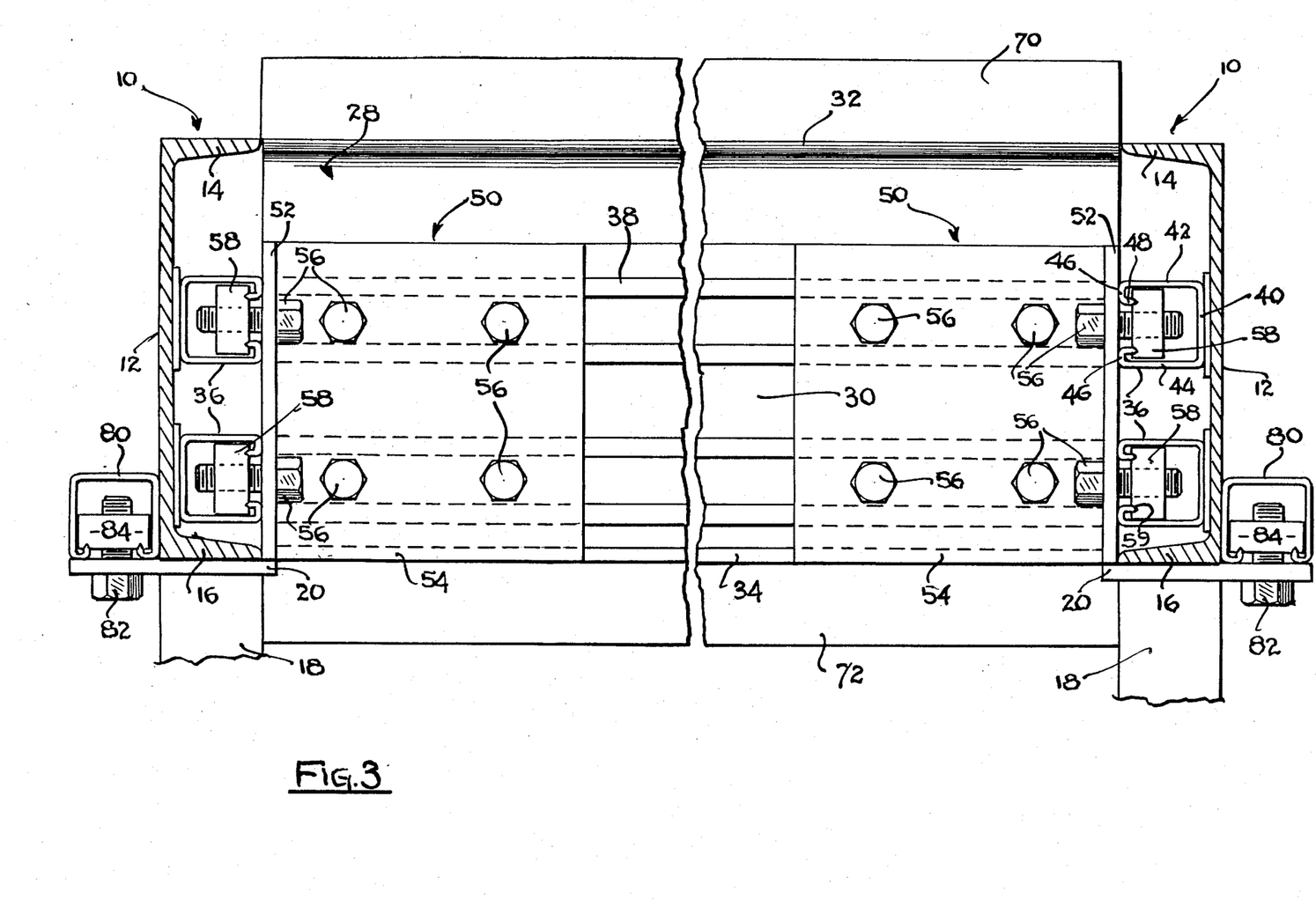
FIG. 3 is an end elevational view of the support structure taken along line 3—3 of FIG. 2.

These framing channels 36 and 38 are often sold under the commercial designation "Uni-Strut". The framing channels each preferably adopt the form of a somewhat C-shaped channel which is provided at the free ends of the horizontally disposed flange portions thereof with vertically disposed tabs, much in the manner as illustrated in FIG. 3. Thus, each framing channel comprises a vertically disposed leg 40 connected by upper and lower plates 42 and 44 and each of which are, in turn, provided with vertically disposed downwardly and upwardly projecting flanges 46. The flanges 46 are each integrally provided with in-turned tabs 48, for reasons which will presently more fully appear. The exact construction of the framing channels generally depends upon the source thereof. The framing channels 36 and 38 are generally provided with the X-ray apparatus and therefore may differ depending upon the source of the X-ray apparatus.

The I-beams are sized so that the ends thereof are slightly spaced from or abut the upper and lower flanges 14 and 16 of the beams 10. An L-shaped bracket 50 which forms part of the positioning-locking means has one plate 52 thereof abutted against the framing channels 36 and the perpendicular plate 54 thereof abutted against the framing channels 38. In this way, the second beams 28 can be shifted along the first beams transversely thereof. Moreover, they are guided in their horizontal movement by virtue of the bracket 50 supported by the framing channels 36 and 38. When the various spaced apart second beams 28 are properly positioned so as to accommodate the X-ray apparatus, they may be secured in that position by fastening means, which may adopt the form of bolts 56 and nuts 58. Thus, and by reference to FIG. 1, it can be observed that the brackets 50 are secured in their positions by means of the various bolts 56 and nuts 58. These bolts secure the plates 52 and 54 and are threadedly received within the nuts 58 which are captured by the flanges 46 of the framing channels.

The nuts 58 are preferably of non-circular shape e.g. square or hexagonal shape, although they should have flat peripheral wall sections. Furthermore, each of the nuts have groves 59 on a side wall thereof and which are located and sized to receive the in-turned tabs 48. In this way the nuts 58 are tightly captured and held within proper alignment in the framing channels.

It can be observed that a separate positioning-locking mechanism may be provided for each of the I-beams 28 at each of their opposite ends. In addition, the framing channels could be welded to the various first and second beams at the factory and provided in a form where they are completely secured to the respective beams at the on-site location. Otherwise, they could be bolted to the respective beams on delivery at the on-site location.

Figure 2:
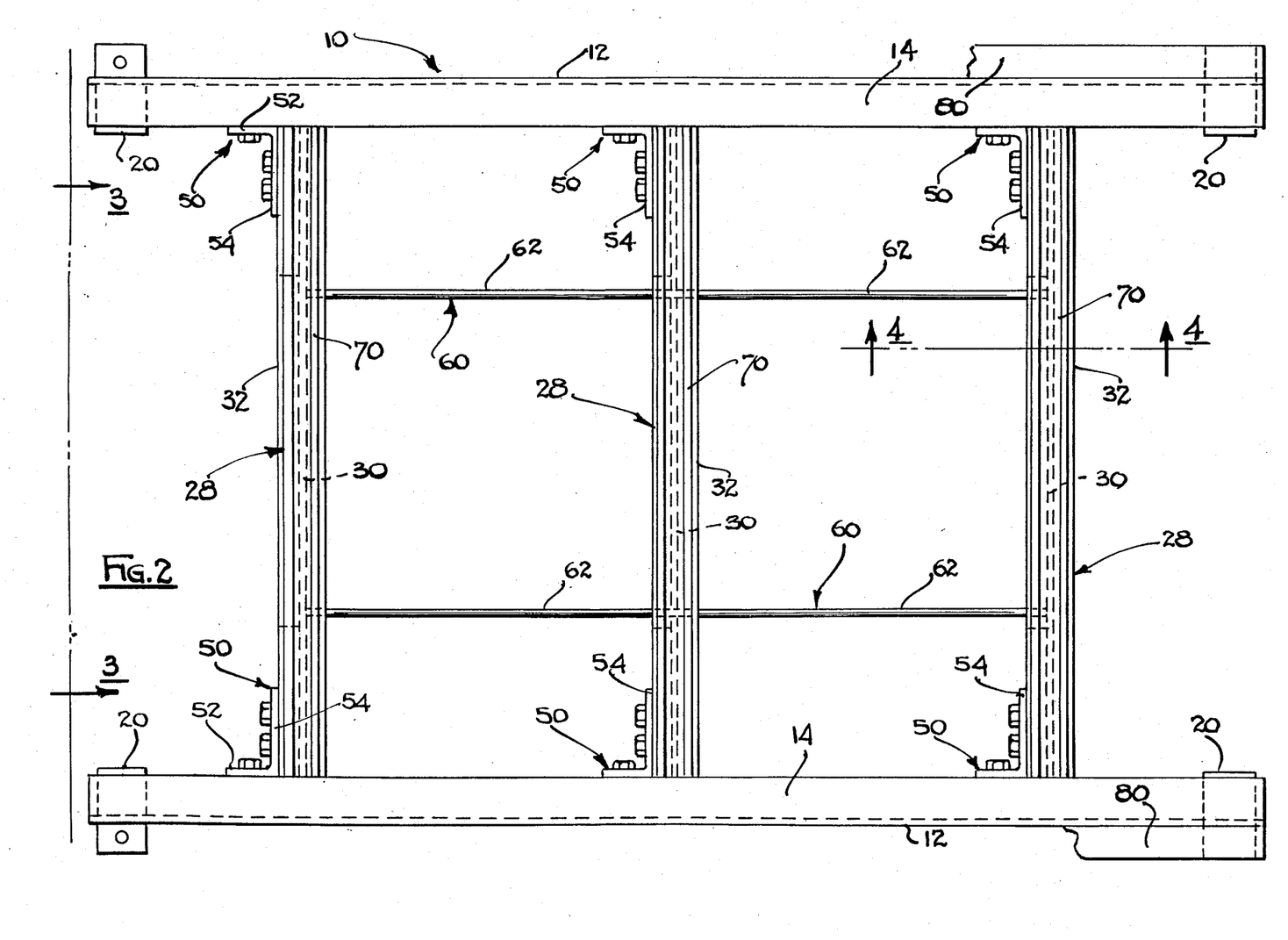
FIG. 2 is a top plan view of the assembled X-ray apparatus support structure FIG. 1.
Figures 4, 6:
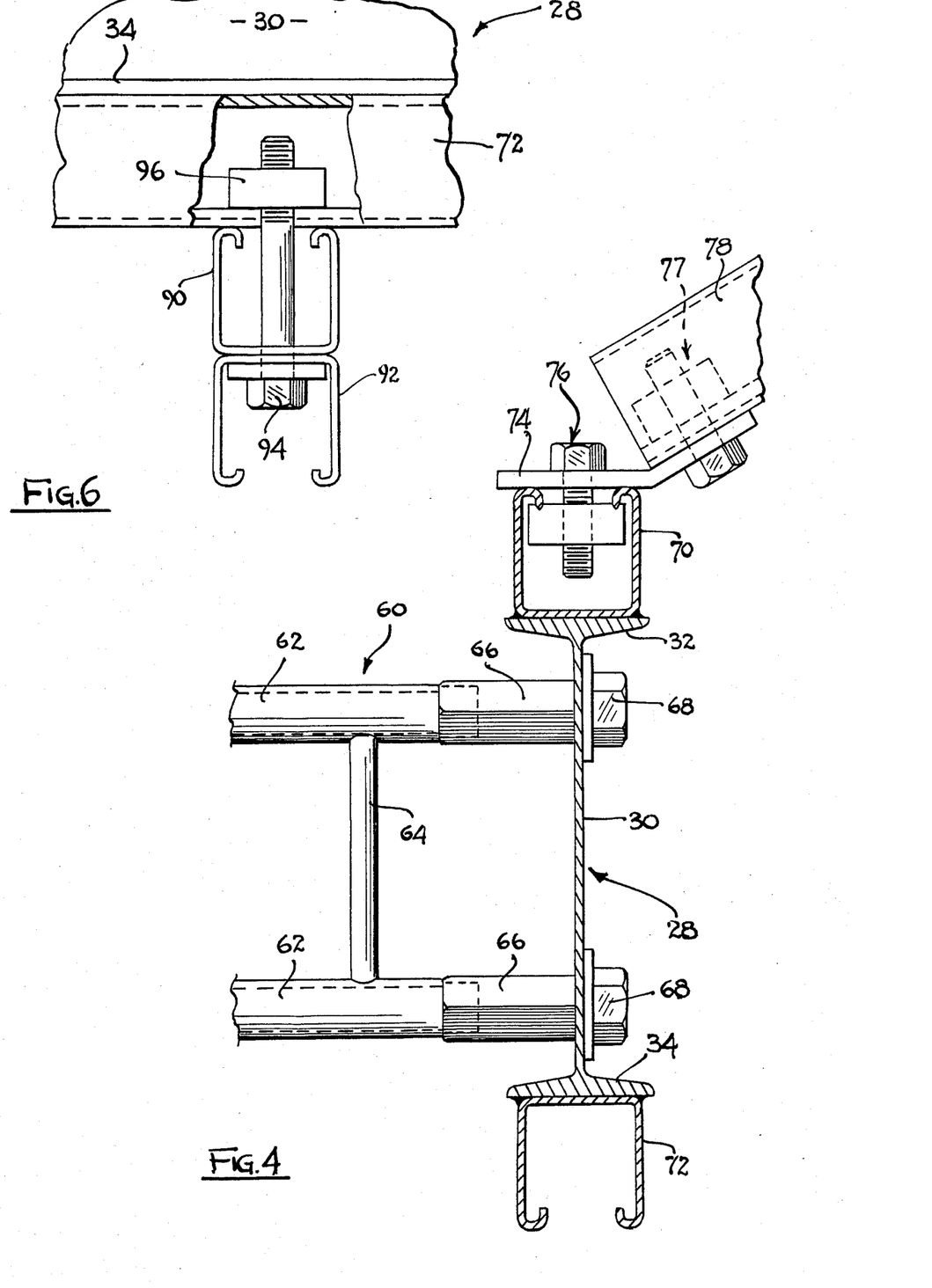
FIG. 4 is a fragmentary view taken along line 4—4 of FIG. 2 and showing a reinforcing assembly forming part of the support structure of the present invention.
FIG. 6 is a fragmentary end elevational view taken along the plane of line 6—6 of FIG. 5 and showing some of the detail of the alternate support structure of FIG. 5.

The support structure of the present invention also comprises one or more stiffener assemblies 60 which are provided for longitudinal extension between each of the second beams 28, in the manner as illustrated in FIGS. 1, 2 and 4 of the drawings. These stiffener assemblies are more fully illustrated in FIG. 4 of the drawings and generally comprise a pair of vertically spaced apart longitudinally extending tubular rods 62 which are inter-connected by vertically extending spacers 64. Each of the rods 62 are provided at their transverse ends with hexagonally shaped tube sections 66 and which are, in turn, bolted to the webs 30 of the spaced apart second beams 28 by means of bolts 68, or similar mechanical fasteners. Thus, after the I-beams 28 have been secured in their desired position to the first pair of spaced apart beams 10, the stiffner assemblies 60 may be connected between each of the pairs of second beams 28. The actual longitudinal dimensions of the stiffener assemblies can be adjusted by merely twisting the rectangularly shaped tube sections 62 on each of the ends thereof to the desired positions and thereafter securing the stiffner assemblies in place by means of the fasteners 68. The threaded connections between the tubular end sections 66 and the rods 62 enables adjustment of the desired lengths thereof.

Framing channels 70 and 72 are secured to the upper and lower flanges 32 and 34 of the second beams 28, in the manner as illustrated in FIGS. 3 and 4 of the drawings. The framing channels 72 on the lower flanges are designed to carry the X-ray apparatus. The X-ray apparatus is generally provided with some mechanism (not shown) for mounting to the framing channels 72 on the pair of spaced apart I-beams 28.

The framing channels 70 enable the support structure of the present invention to be secured to a ceiling joist or like structure. For this purpose, an angle clip 74 may be secured to the framing channel 70 by means of a bolt and nut arrangement 76 and which is similar to previously described bolts 56 and nuts 58. An angle brace 78, which may be in the form of a standard framing channel, is also bolted to the angle clip 74, in the manner as illustrated in FIG. 4. This angle brace may then be secured to a ceiling joist or similar portion of the ceiling structure for further stablizing the support structure of the present invention. It should be recognized that a similar bolt and nut arrangement 76 is employed for securing the angle brace 78 to the angle clip 74.

The framing channels 70 and 72 are substantially identical to the previously described framing channels 36 and 38. Moreover, the exact form of the framing channel may vary depending upon the source of the X-ray apparatus, as previously described. The framing channels 70 and 72 are also preferably welded to the various I-beams 28 at a factory source. However, they can be provided separately along with mechanical fasteners for securement to the I-beams at the on-site location.

It may be appreciated that every installation, to some extent, is unique to the structure which supports the X-ray apparatus. Moreover, the exact structure which is employed depends on the contruction of the X-ray apparatus. Nevertheless, the support system of the present invention is highly unique in that it is adaptable to almost all types of conventional X-ray apparatus. The crane section of the X-ray apparatus may be easily secured to the framing channels 72 on the underside of each of the second beams 28. In addition, the support structure of the present invention does not necessarily need a reinforced ceiling or the like for support inasmuch as it is capable of being free standing on a floor or similar supporting surface.

The various components forming part of the support structure may be pre-cut at the factory location, given the specifications of the installation site. Thus, all that is required is generally the overall dimensions and the mode of construction of the installation site such that the various components forming part of the support structure can be cut to and provided in the proper sizes.

The support structure of the present invention may also be provided with struts 79 for bolting or other securement to the beam 10 and for securement to the ceiling or similar overhead surface, if desired, at the on-site location. These struts 79 may be provided with base plates angularly located at the ends of the struts so that they can extend angularly outwardly and upwardly from the various first beams 10 in the manner as illustrated in FIG. 1.

The first beams 10 are also adapted for moveable positioning with respect to the columns 18 so that a desired spacing can be achieved between those columns 18 supporting each of the first beams 10. When the desired spacing has been achieved, the first beams are locked to the columns. For this purpose, additional framing channels 80 are secured to the exterior face of each of the first beams adjacent the lower ends thereof. These framing channels 80 are substantially identical to the previously described framing channels 36 and 38. Bolts 82 and nuts 84 are also provided for securing the framing channels 80 and hence the first beams 10 to the head plates 20. In this way, the first beams 10 can be re-positioned with respect to the columns 18 without the necessity of re-drilling holes in the head plates 20.

Figure 5:
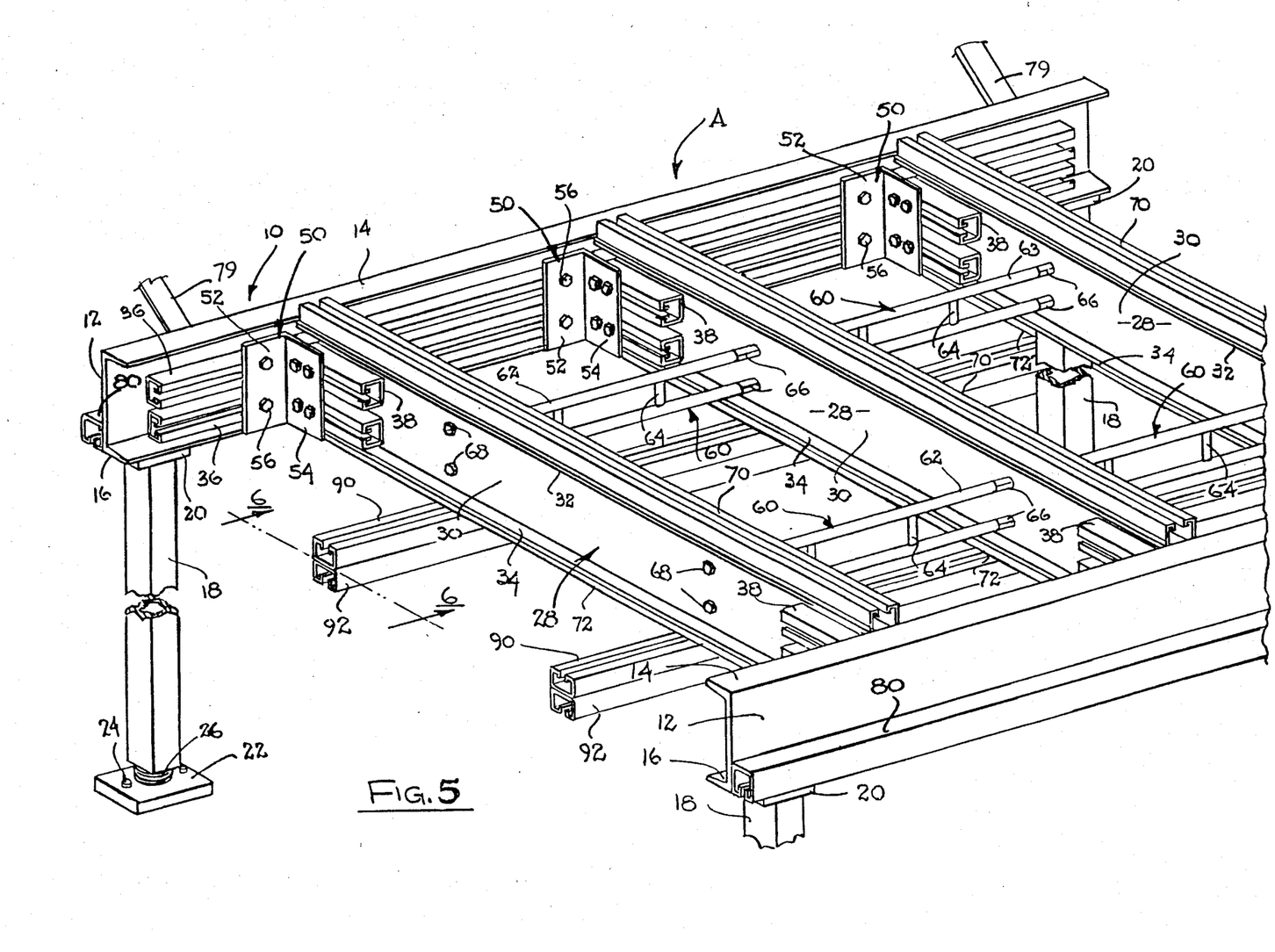
FIG. 5 is a fragmentary perspective view, somewhat similar to FIG. 1, and showing an alternate support structure for suspending an X-ray apparatus and enabling movement in a longitudinal direction, also constructed in accordance with and embodying the present invention.

In certain installations, the available width of the room or other location which is to receive the support structure may not be sufficient to accommodate the embodiment as illustrated in FIG. 1. Thus, the X-ray apparatus may be adapted for traveling longitudinally on the support structure as opposed to transversely on the support structure of FIG. 1. In this case, individual pairs of framing channels 90 and 92 could be secured to the underside of the framing channels 72 by means of bolts 94 and nuts 96 as shown in FIGS. 5 and 6. Here again, the bolts 94 are similar to the previously described bolts 56 and the nuts 96 are similar to the previously described bolts 58.

The two framing channels 90 and 92 are inverted relative to one another so that the legs 40 are disposed in abutted position, as illustrated. The bolts 94 are designed to extend through apertures drilled or otherwise formed in the abutted legs 40. In this way, it can be observed that the X-ray apparatus can be adapted for securement to the lower longitudinally extending framing channel 92 for shiftable movement longitudinally of the support structure. The framing channels 90 and 92 could also be spaced at a distance of about two feet from each other so as to conform to the spacing between overhead ceiling trusses.

It should also be understood that additional I-beams could be welded or otherwise secured to the underside of the I-beams 28 and extended in a longitudinal direction with additional framing channels secured to the underside of these longitudinally extending I-beams. In each case, the components would be cut to the desired size at the factory and shipped for assembly at the on-site location.

Second beams 28 could be eliminated and a pair of additional I-beams 86 welded thereto in the manner as illustrated in FIG. 5. The framing channels could also be secured to the I-beams 86 or otherwise, the I-beams 86 could be adapted for receiving the X-ray apparatus. Nevertheless, it can be observed that the X-ray apparatus can be adapted for securement to the supporting structure for shiftable movement both longitudinally of the support structure or transversely of the support structure.

Thus, there has been illustrated and described a unique and novel support structure which may be prefabricated and erected at an on-site location and which therefore fullfills all of the objects and advantages which have been sought. It should be understood that many changes, modifications, variations and other uses and applications will become apparent to those skilled in the art after considering this specification and the accompanying drawings. Therefore, any and all such changes, modifications, variations, and other uses and applications, which become apparent to those skilled in the art, after considering this specification and the accompanying drawings, are deemed to be covered by the invention.

Having thus described my invention, what I desire to claim and secure by Letters Patent is:

1. A free standing X-ray apparatus support structure for movably supporting an X-ray apparatus, said support structure comprising:
    (a) a pair of first beams extending generally parallel in a first direction,
    (b) a plurality of second beams extending between the pair of first beams and being supported thereby, said second beams being generally parallel to one another in a second direction,
    (c) a plurality of columns disposed in generally upright positions and supporting said first and second beams in generally horizontally disposed positions, said columns being disposed on and supported by a floor or similar horizontally disposed supporting surface,
    (d) a first frame member secured to each of said first beams,
    (e) a second frame member secured to each of said second beams said beams located at substantially the same horizontal location as said first frame members cooperating with said frame members to enable said second beams to be movable with respect to said first beams, and
    (f) means for locking said second beams in a desired position with respect to said first beams when a desired spacing has been achieved between said second beams.

2. The X-ray apparatus support structure of claim 1 further characterized in that a separate bracket extends between a first frame member and a second frame member to enable said means for locking to lock the second beams with respect to the first beams.

3. The X-ray apparatus support structure of claim 1 further characterized in that first mechanical fasteners secure said first beams to said columns and second mechanical fasteners secure said second beams to said first beams.

4. The X-ray apparatus support structure of claim 1 further characterized in that said first beams are C-channels and said second beams are I-beams.

5. The X-ray apparatus support structure of claim 4 further characterized in that said frame members are each somewhat C-shaped channels.

6. The X-ray apparatus support structure of claim 1 further characterized in that said support structure is rectangularly shaped and is comprised of four upright columns.

7. The X-ray apparatus support structure of claim 6 further characterized in that the height of each of said columns is vertically adjustable.

8. A kit for assembling a free standing X-ray apparatus support structure, said kit comprising:
    (a) a plurality of columns capable of being located in an upright position and being pre-cut to desired dimensions,
    (b) a plurality of beams capable of being disposed on and supported by said columns in generally horizontally disposed positions, said beams also being pre-cut to desired dimensions,
    (c) fastening means for securing certain of said beams to said columns, (d) means for enabling certain of said beams to be movable relative to other of said beams when disposed on such columns and being secured in a selected position relative to said other of said beams when in the selected position, and (e) framing channels for securement to the underside of certain of said beams to receive and support an X-ray apparatus.

9. The kit of claim 8 further characterized in that said kit comprises additional fastening means for securing certain of said beams to the other of said beams when in desired horizontal positions.

10. The kit of claim 8 further characterized in that said kit comprises stiffening members capable of being connected between two of said spaced apart beams.

11. The kit of claim 8 further characterized in that said certain of said beams and said other of said beams are adapted to be generally perpendicularly arranged relative to one another.

12. The kit of claim 8 further characterized in that the means to enable certain of said beams to be movable relative to other of the beams comprises a plurality of first frame members for securement to certain of the beams and a plurality of second frame members for securement to some of the other beams.

13. A support structure for movably supporting an X-ray apparatus, said support structure comprising:

(a) a pair of first beams extending generally parallel in a first direction.

(b) a plurality of second beams extending between the pair of first beams and being supported thereby, said second beams being generally parallel to one another in a second direction, (c) a plurality of columns disposed in generally upright positions and supporting said first and second beams in generally horizontally disposed positions, said columns being disposed on and supported by a floor or similar horizontally disposed supporting surface, (d) means for enabling certain of said second beams to be movable relative to said first beams when disposed on said columns which are secured when in the selected position, (e) first framing channels secured to the underside of certain of said second beams and capable of supporting an X-ray apparatus, and (f) second framing channels secured to the upper surface of said certain of said second beams for supporting portions of said X-ray apparatus.

14. The X-ray apparatus support structure of claim 13 further characterized in that first mechanical fasteners secure said first beams to said columns and second mechanical fasteners secure said second beams to said first beams.

15. The X-ray apparatus support structure of claim 13 further characterized in that said first beams are C-channels and said second beams are I-beams.

16. The X-ray apparatus support structure of claim 15 further characterized in that said frame members are each somewhat C-shaped channels.

17. The X-ray apparatus support structure of claim 13 further characterized in that the means for enabling certain of said beams to be movable comprises:

(a) a first frame member secured to each of said first beams, (b) a second frame member secured to each of said second beams and being located at substantially the same horizontal elevation as said first frame member and cooperating with said first frame member to enable said second beams to be movable with respect to said first beams, and (c) means for locking said second beams in a desired position with respect to said first beams when a desired spacing has been achieved between said second beams.

18. A method for assembling a free standing X-ray apparatus support structure at an on-site location, said method comprising;

(a) erecting a plurality of columns in a selected pattern in upright disposition, (b) securing a plurality of first beams which are pre-cut to a desired size to the plurality of columns in a certain horizontal arrangement, (c) locating a plurality of second beams which are pre-cut to a desired size with respect to the plurality of first beams and in a certain horizontal arrangement, (d) movably positioning at least one of the second beams with respect to another one of the second beams to obtain a desired spacing therebetween sufficient to support an X-ray apparatus, and (e) securing the second beams to the first beams when in the desired spacing.

19. The X-ray apparatus support structure of claim 18 is further characterized in that the method comprises securing a spacing structure between the spaced apart second beams.

20. The X-ray apparatus support structure of claim 18 is further characterized in that the method comprises:

(a) securing a first frame member to each of said first beams, (b) securing a second frame member to each of said second beams and which is located at substantially the same horizontal position as said first frame members and co-operating with said first frame members to enable said second beams to be movable with respect to said first beams.

* * * * *